United States Patent [19]

Maini et al.

[11] Patent Number: 5,719,327
[45] Date of Patent: Feb. 17, 1998

[54] SAND PACK HOLDER

[75] Inventors: Brij Bhooshan Maini; Fausto Cesare Nicola, both of Calgary, Canada

[73] Assignee: Alberta Oil Sands Technology and Research Authority, Edmonton, Canada

[21] Appl. No.: 208,242

[22] Filed: Mar. 9, 1994

[51] Int. Cl.⁶ .................................................. G01N 15/08
[52] U.S. Cl. .................................................. 73/38; 73/794
[58] Field of Search ........................... 73/38, 865.6, 794

[56] References Cited

U.S. PATENT DOCUMENTS

| | | | |
|---|---|---|---|
| 3,638,478 | 2/1972 | Dietert et al. | 73/38 |
| 4,149,407 | 4/1979 | Strom et al. | 73/794 |
| 4,478,069 | 10/1984 | Zuckerwar | 73/38 |
| 4,562,726 | 1/1986 | Barnaby | 73/38 |
| 4,562,727 | 1/1986 | Dilgren et al. | |
| 4,572,009 | 2/1986 | Brauer et al. | |
| 4,599,891 | 7/1986 | Brauer et al. | 73/38 |
| 4,688,238 | 8/1987 | Sprunt et al. | 73/38 |
| 4,799,382 | 1/1989 | Sprunt et al. | 73/38 |
| 4,868,751 | 9/1989 | Dogru et al. | |
| 5,297,420 | 3/1994 | Gilliland et al. | 73/38 |
| 5,325,723 | 7/1994 | Meadows et al. | 73/794 |

Primary Examiner—George M. Dombroske
Assistant Examiner—Eric S. McCall
Attorney, Agent, or Firm—Millen, White, Zelano, & Branigan, P.C.

[57] ABSTRACT

A sand pack holder is provided for testing the properties of a sand sample or testing the performance of an oil recovery process in the sample. The sample is pressurized within the holder to simulate reservoir condition. The holder comprises: a housing forming an open-ended longitudinal bore; a tubular, radially deformable or expandable sleeve extending through the bore in spaced relation with the housing sidewall, so an annulus is formed; a sand sample packed in the annulus; sealable open ends of the annulus and the sleeve passageway; ports formed at each end of the annulus so that pressurized fluid may be injected into the sand sample at one end and discharged from the other; a port for injecting pressurized fluid into the sleeve passageway to radially expand the sleeve to compressively load the sand pack against the housing sidewall; the housing sidewall forming a plurality of measurement ports communicating with the annulus; and measurement devices, such as pressure probes, having hollow stems threaded into the measurement ports, the stems having sand exclusion screens at their inner ends for preventing sand ingress. By locating the sand pack in the annulus instead of in the deformable sleeve, the measurement devices need to connect only with the housing instead of with the sleeve. The need for flexible connections is obviated and measurement ports can be readily accessed.

4 Claims, 3 Drawing Sheets

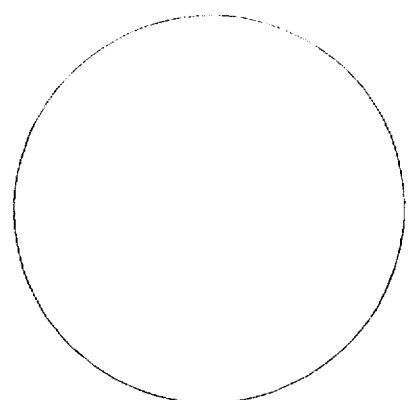
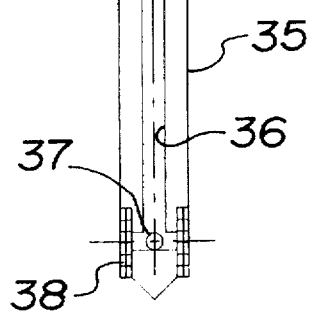
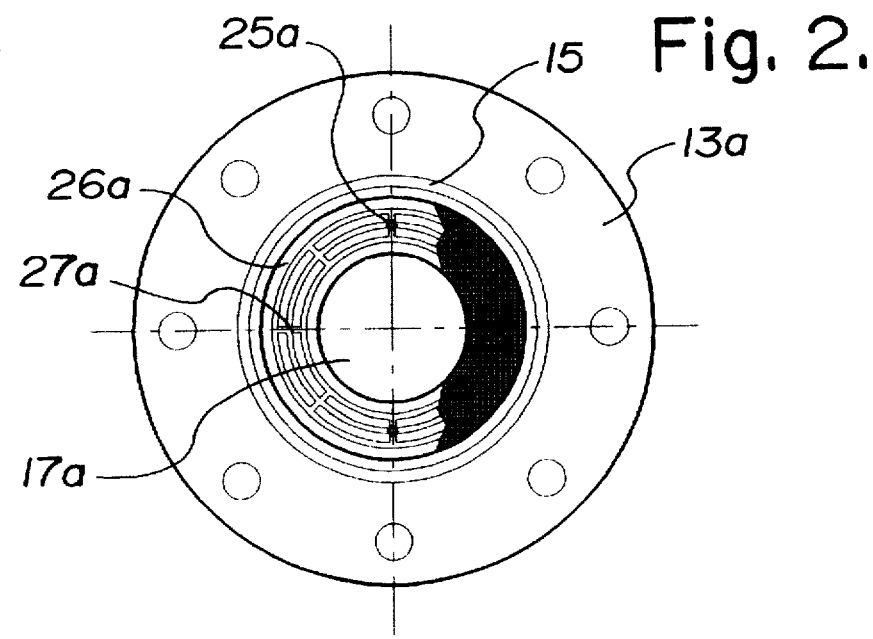
Fig. 3.
Fig. 2.

SAND PACK HOLDER

FIELD OF THE INVENTION

The present invention relates to laboratory testing equipment, referred to as a sand pack holder, for use in measuring the properties of a sand or glass bead sample or for testing a process in the sample. The holder is designed to enable application of compressive pressure to the sample, to simulate reservoir overburden pressure.

BACKGROUND OF THE INVENTION

Sand pack holders are commonly used in oil industry laboratories to measure properties of a sand or glass bead sample or to test a recovery process in the sample. The sample is commonly referred to as a "sand pack".

In general, fluid is driven through the sand pack and measurements are taken, for example of the pressure, at spaced points along its length. The measurement data provides a basis for establishing the sought for information.

It is desirable to apply compressive pressure to the sand pack during the duration of the test, to simulate reservoir pressure conditions.

A typical prior art sand holder is disclosed in U.S. Pat. No. 4,599,891, issued Jul. 15, 1986, to Brauer et al. The sand pack is contained within a resilient, elastomer, tubular sleeve positioned within the bore of a housing. The sidewall of the housing is spaced from the sleeve to form an annulus. Plug means close the ends of the sleeve and of the annulus. Ports are provided in the plug means for injecting fluid into one end of the sand pack and discharging it from the other. The housing sidewall forms a port through which pressurized fluid may be introduced into the annulus to compress the sleeve and its contained sand pack, thereby simulating reservoir overburden pressure. Measurement port means extend through the housing sidewall and sleeve wall, to enable measurement devices, such as pressure probes, to communicate with the sand pack.

There are two disadvantages that arise from this prior art design. Firstly, because the sleeve moves when compressive pressure is applied or released, it is necessary to fit the measurement port means with flexible joints. These joints are subject to failure. Secondly, the assembly does not lend itself to having a multiplicity of measurement ports, so that some can be initially closed and then opened if required. Each additional port adds substantially to the cost of the device and increases the likelyhood of failure.

SUMMARY OF THE INVENTION

The present invention provides a sand pack holder which eliminates the need for flexible joints for connecting the measurement ports with the sleeve.

More particularly, in a preferred form the holder comprises:

- a housing which forms an open-ended longitudinal bore;
- a tubular sleeve formed of deformable material, such as lead, so that the sleeve will expand radially when pressurized from within;
- the sleeve being generally coextensive with the housing bore and being positioned to extend longitudinally therein in generally coaxial arrangement, the sleeve being inwardly spaced from the housing sidewall, so as to combine therewith to form an annulus;
- a sand pack positioned in the annulus;
- plug means for sealing the open ends of the annulus and the sleeve passageway;
- the plug means and the housing combining to form a housing assembly;
- the housing assembly forming first port means for introducing pressurized fluid into one end of the annulus, second port means for discharging fluid from the other end of the annulus and third port means for introducing pressurized fluid into the sleeve passageway to expand the sleeve to radially compress the sand pack against the housing sidewall;
- the housing sidewall forming measurement ports communicating with the annulus at points spaced along its length; and
- a plurality of measurement devices, each having a rigid stem having means for excluding sand at its inner end and being associated with one of the measurement ports so that it communicates with the sand pack.

The main features of the invention are as follows:

- the chamber for containing the sand pack is the annulus formed between the housing and the internally pressurized sleeve;
- the measurement ports are formed only in the housing sidewall and do not penetrate the sleeve, so that flexible fittings can be eliminated from the port structure; and
- the stems of the measurement devices are preferably protected by means such as screens against incursion by the pressurized sand.

Broadly stated, the invention is a sand pack holder adapted to simulate reservoir overburden pressure on a contained sand pack, comprising: a housing having a sidewall forming an open-ended, longitudinal bore; a radially expandable, tubular sleeve being generally coextensive with the housing bore and adapted to extend therein in radially spaced relationship with the housing sidewall to form an annulus therebetween for receiving the sand pack, said sleeve forming an open-ended longitudinal passageway; said housing and sealing means combining to form a housing assembly; said housing assembly forming first port means at one end for introducing pressurized fluid into one end of the annulus, second port means at the other end for discharging fluid from the other end of the annulus and third port means for introducing pressurized fluid into the sleeve passageway to expand the sleeve to radially compress the sand pack against the housing sidewall; and the housing sidewall forming measurement ports communicating with the annulus at points spaced apart along its length.

BRIEF DESCRIPTION OF THE DRAWINGS

FIG. 2 is an end view of the distribution cap, which seals one end of the annulus;

FIG. 3 is a side sectional view of a pressure probe having a sand exclusion screen;

DETAILED DESCRIPTION OF THE PREFERRED EMBODIMENT

Figure 1:
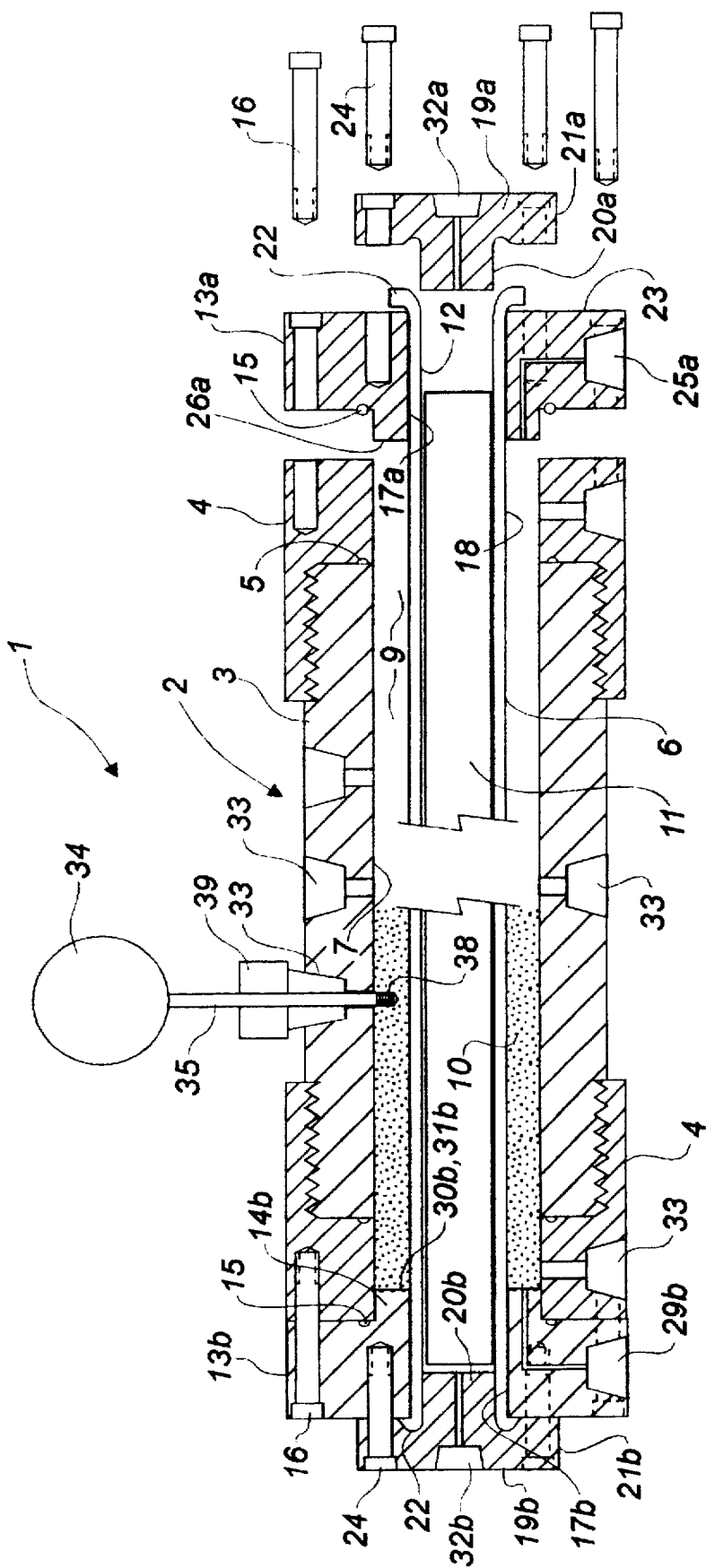
FIG. 1 is a longitudinal sectional view of the sand pack holder, one end being assembled, the other end being exploded to show the pre-assembly flaring of the sleeve.
Figure 4:
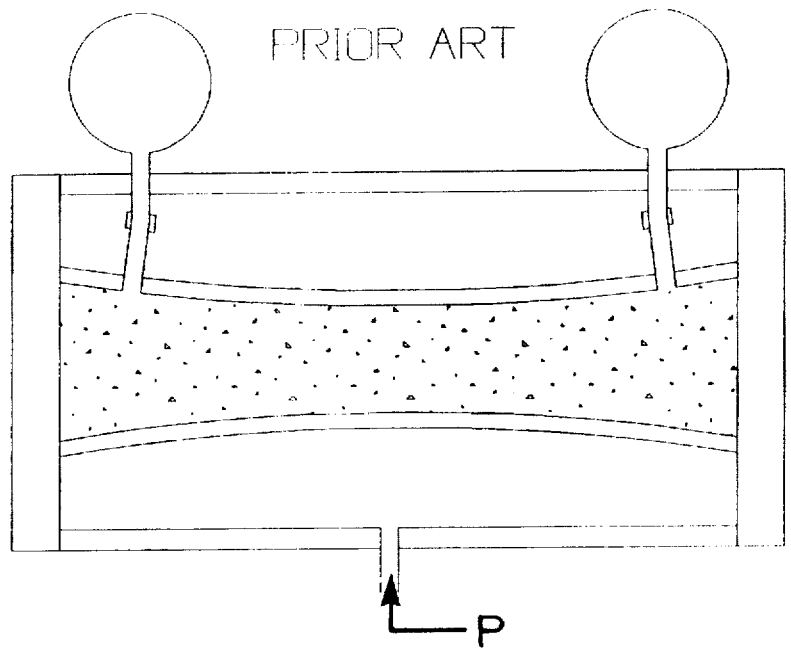
FIG. 4 is a simplified sectional schematic view of a sand pack holder in accordance with the prior art, showing exaggerated sleeve deformation due to exterior compressive pressure and bending of the flexible stem of a pressure probe.
Figure 5:
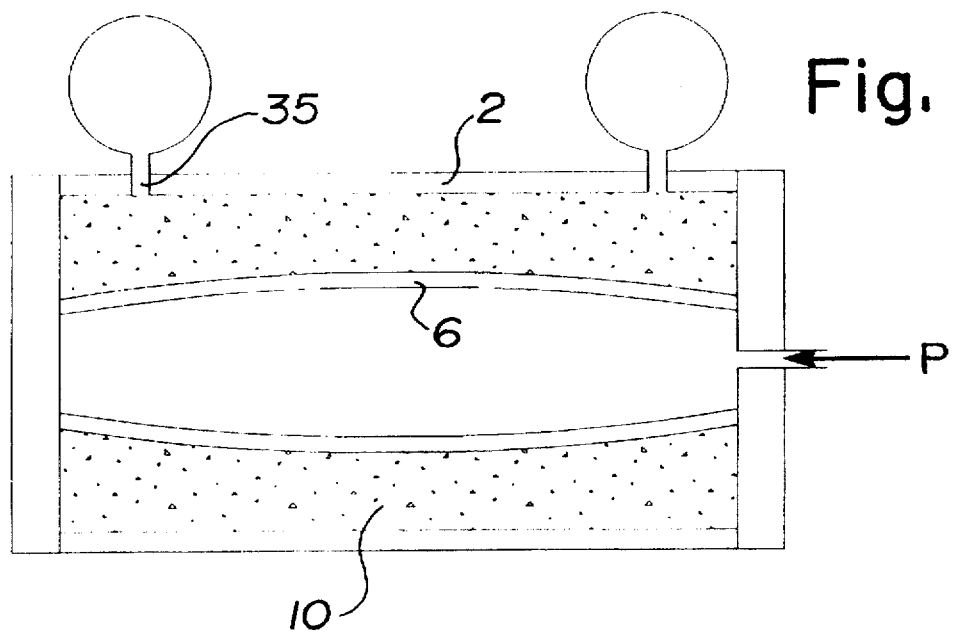
FIG. 5 is a simplified sectional schematic view of la sand pack holder in accordance with the invention, showing exaggerated sleeve deformation due to interior compressive pressure.

Referring to FIG. 1, the sand pack holder 1 comprises a cylindrical, tubular housing 2 consisting of a tube 3 and end flanges 4 threaded thereon. An O-ring seal 5 seals between each flange 4 and the tube 3.

A radially expandable, deformable, tubular sleeve 6 extends through the housing bore 3. The sleeve 6 is cylindrical and generally concentric with the bore 3. It is spaced inwardly from the inner surface 7 of the housing sidewall 8, so that an annulus 9 is formed theresbetween. The ends of the sleeve 6 extend out of the housing bore 3.

The sleeve 6 is formed of lead, which is conventionally used for this application. The material can deform sufficiently without rupturing so as to enable the required compression described below. The lead can be used at elevated temperatures up to about 500° F. (260° C.).

The sand pack 10 to be tested is tamped into place in the annulus 9.

A support rod 11 is inserted in the passageway 12 formed by the sleeve 6. The support rod 11 is generally coextensive with the sleeve and has a diameter slightly smaller than the diameter of the sleeve passageway 12. The support rod 11 thus functions to hold the sleeve 6 fully open.

Means are provided for sealing the ends of the annulus 9 and the sleeve passageway 12. More particularly, annular caps 13a, 13b are fitted to the end flanges 4 at the ends of the housing 2. Each cap 13a, 13b has an inner ring portion 14a, 14b that extends into the annulus 9 and has a close fit with the housing sidewall 8. Each cap 13a, 13b is sealed to the adjacent end flange 4 by a seal ring 15. Bolts 16 secure each cap 13a, 13b to its associated housing flange 4. The caps 13a, 13b each have a bore 17a, 17b that is dimensioned to closely fit the outside surface 18 of the sleeve 6. Plugs 19a, 19b close the open ends of the sleeve 6. Each plug 19a, 19b comprises an inner nose portion 20a, 20b, which closely fits into the sleeve passageway 12, and an enlarged portion 21a, 21b. Each end 22 of the sleeve 6 is outwardly flared to abut the end surface 23 of its associated cap 13a, 13b. The associated plug's enlarged portion 21a, 21b clamps the sleeve end 22 against the cap end surface 23. Bolts 24 secure each plug 19a, 19b firmly against the end surface 23 of its associated cap 13a, 13b. Thus the plugs 19a, 19b function to seal the ends of the passageway 12.

Fluid injection ports 25a extend through the cap 13a to the inner end face 26a of the nose portion 20a. As shown in FIG. 2, an interconnected grid 27a of grooves 28a, formed in the face 26a, communicate with the ports 25a. The grid 27a distributes injected fluid uniformly across the adjacent end face of the sand pack 10.

Fluid discharge ports 29b extend through the other cap 13b. The discharge ports 29b also communicate with a grid 30b of grooves formed in the inner end face, 31b of the nose portion 20b.

In operation, means (not shown) are provided for injecting pressurized fluid into the sand pack 10 through the injection ports 25a and grid 27a during testing. Means (also not shown) are provided to collect fluid exiting through the discharge ports 29b.

Pressurization ports 32a, 32b extend through the plugs 19a, 19b. Means (not shown) are provided for injecting pressurized fluid through the ports 32a, 32b into the sleeve passageway 12 to cause the sleeve 6 to expand radially and compress the sand pack 10, to subject it to simulated overburden pressure.

Thus fluid can be injected through the injection ports 25a to sweep through the pressurized annular sand pack 10 and discharge through the discharge ports 29b, and the sleeve 6 can be internally pressurized to compress the sand pack 10 in the annulus 9 to subject it to simulated overburden pressure.

A plurality of threaded measurement ports 33 extend through the sidewall 8 of the housing 2, to communicate with the annulus 9 and the sand pack 10 contained therein. The ports 33 are spaced along the length of the housing tube 3.

Pressure probes 34 are positioned in ports 33 to monitor conditions in the sand pack 10. As shown in FIG. 3, each probe 34 is provided with a rigid stem 35 having a longitudinal bore 36 and laterally opening apertures 37. A screen 38 is mounted to the stem 35 to cover the apertures 37 to prevent the ingress of sand. A threaded compression fitting 39 secures the stem 35 in the port 33.

The embodiments of the invention in which an exclusive property or privilege is claimed are defined as follows:

1. A sand pack holder adapted to simulate reservoir overburden pressure on a contained sand pack, comprising:

a housing having a sidewall forming an open-ended longitudinal bore and first and second ends;

a radially expandable, tubular sleeve being generally co-extensive with the housing bore and extending therethrough in radially spaced relationship with the housing sidewall to form an annulus having a length and first and ,second ends therebetween for receiving the sand pack, said sleeve forming an open-ended longitudinal passageway;

means for sealing the open ends of the annulus and the sleeve passageway;

said housing and sealing means combining to form a housing assembly;

said housing assembly forming first port means at the first end for introducing pressurized fluid into the first end of the annulus, second port means at the second end of the housing for discharging fluid from the second end of the annulus and third port means for introducing pressurized fluid into the sleeve passageway to expand the sleeve to radially compress the sand pack against the housing sidewall;

the housing sidewall forming a plurality of measurement ports communicating with the annulus at points spaced along the length of the annulus; and a plurality of measurement devices, each having a rigid stem forming a longitudinal bore and having means at an inner end thereof for excluding sand from the bore and being associated with one for the measurement ports so that the bore communicates directly with the annulus.

2. The sand pack holder as set forth in claim 1 wherein:

the housing bore, sleeve and sleeve passageway are all generally cylindrical in configuration and the sleeve is generally concentric with the housing bore, and comprising a rod for insertion in the sleeve passageway, said rod being generally coextensive with the sleeve, for maintaining the sleeve fully extended, said rod having a diameter smaller than but close to the inner diameter of the sleeve.

3. The sand pack holder as set forth in claim 1 comprising:

a sand pack positioned in the annulus.

4. The sand pack holder as set forth in claim 2 comprising:

a sand pack positioned in the annulus.

\* \* \* \* \*